United States Patent
Naidu

(10) Patent No.: US 6,638,974 B1
(45) Date of Patent: Oct. 28, 2003

(54) ASCORBYL ESTERS FOR THE TREATMENT OF CANCER

(75) Inventor: Kamatham A. Naidu, Carrollton, TX (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 09/544,693

(22) Filed: Apr. 7, 2000

Related U.S. Application Data

(60) Provisional application No. 60/128,680, filed on Apr. 9, 1999.

(51) Int. Cl.[7] .............................................. A61K 31/34
(52) U.S. Cl. ...................................................... 514/474
(58) Field of Search ......................................... 514/474

(56) References Cited

U.S. PATENT DOCUMENTS

| | | | |
|---|---|---|---|
| 4,439,196 A | 3/1984 | Higuchi | 604/890 |
| 4,447,224 A | 5/1984 | DeCant, Jr. et al. | 604/67 |
| 4,447,233 A | 5/1984 | Mayfield | 604/152 |
| 4,475,196 A | 10/1984 | LaZor | 371/29 |
| 4,486,194 A | 12/1984 | Ferrara | 604/897 |
| 4,487,603 A | 12/1984 | Harris | 604/152 |
| 4,925,678 A | 5/1990 | Ranney | 424/293 |
| 4,959,217 A | 9/1990 | Sanders et al. | 424/473 |
| 5,167,616 A | 12/1992 | Haak et al. | 604/20 |
| 5,169,383 A | 12/1992 | Gyory et al. | 604/20 |
| 5,225,182 A | 7/1993 | Sharma | 424/9 |

FOREIGN PATENT DOCUMENTS

| | | | | |
|---|---|---|---|---|
| EP | 0 875246 A1 | * | 11/1998 | 514/474 |
| JP | 06219944 A2 | * | 8/1994 | 514/474 |

* cited by examiner

*Primary Examiner*—Jerome Goldberg
(74) *Attorney, Agent, or Firm*—Kohn & Associates, PLLC

(57) ABSTRACT

There is provided a method of treating cancer by treating the cancer cells with a lipophilic derivative of ascorbic acid. Also provided is a method of inhibiting the Ras pathway by administering a lipophilic derivative of ascorbic acid. A method of inducing apoptosis in cancer cells is also provided by treating cancer cells with a lipophilic derivative of ascorbic acid. A pharmaceutical composition for the treatment of cancer comprising a lipophilic derivative of ascorbic acid in a pharmaceutically acceptable carrier is also provided.

17 Claims, 19 Drawing Sheets

(4 of 19 Drawing Sheet(s) Filed in Color)

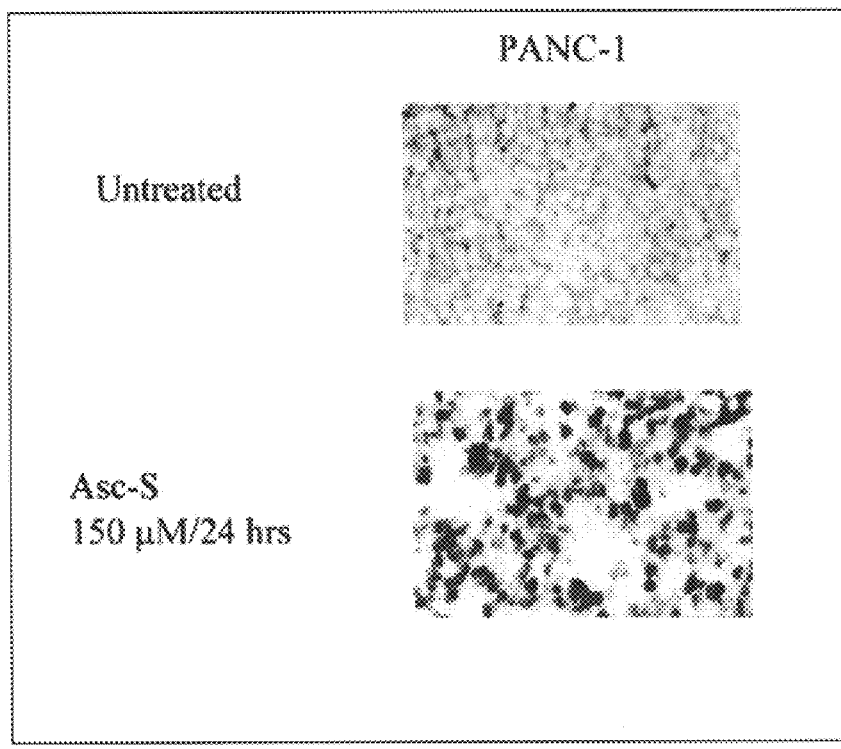

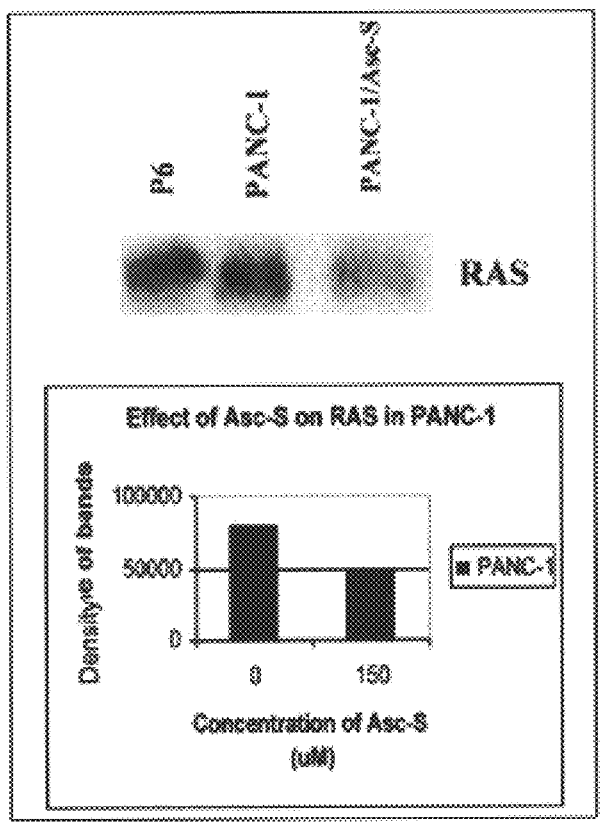
*Figure - 4*
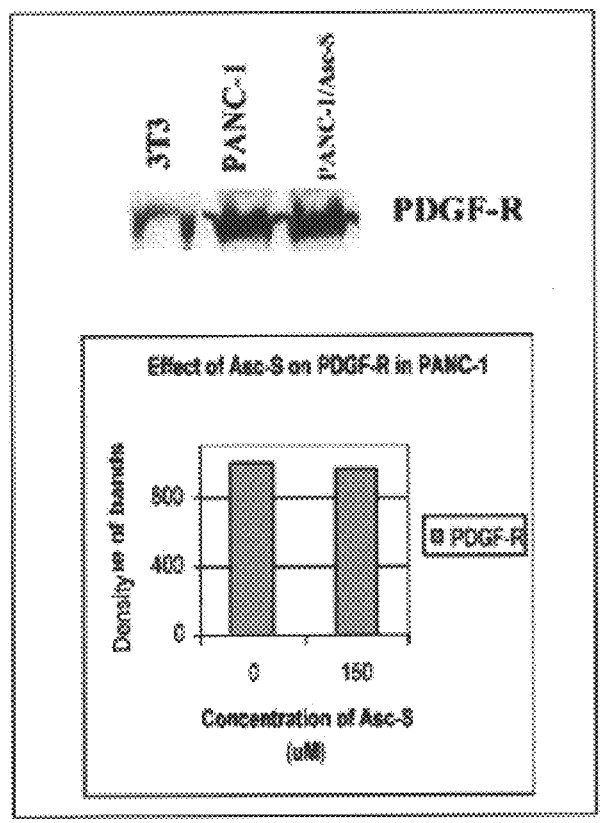
*Figure - 5a*
*Figure - 5b*

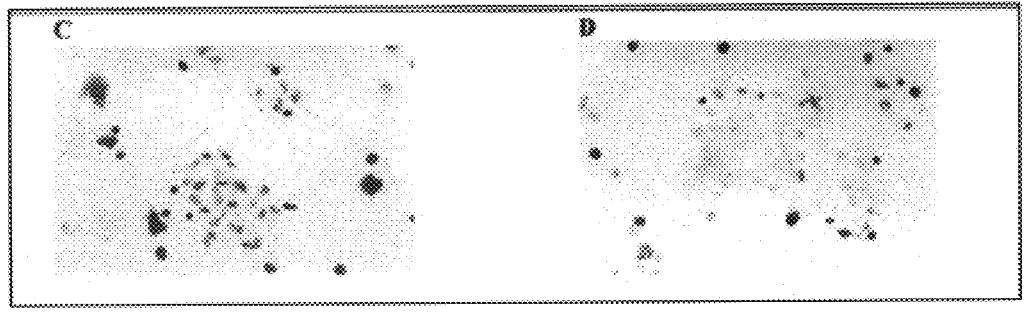
*Figure - 10c*     *Figure - 10d*
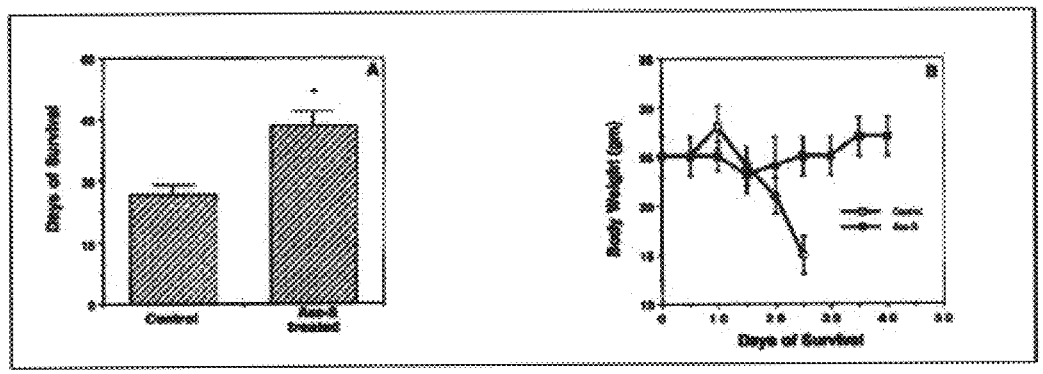
*Figure - 11a*     *Figure - 11b*

ASCORBYL ESTERS FOR THE TREATMENT OF CANCER

CROSS-REFERENCE TO RELATED APPLICATIONS

This is a conversion of U.S. Provisional Patent Application No.: 60/128,680, filed Apr. 9, 1999, incorporated herein by reference.

BACKGROUND OF THE INVENTION

1. Field of the Invention

The present invention relates to a method and composition for treating cancer. More specifically, the present invention relates to the use of lipophilic synthetic derivatives of ascorbic acid, e.g., Ascorbyl stearate and Ascorbyl palmitate in treating cancer cells.

2. Description of Related Art

Pancreatic cancer of ductal type (DAP) is the leading cause of cancer death world wide[1]. This highly aggressive tumor affects patients usually older than 50 years, and its incidence is increasing, particularly in women. This tumor has short median survival, and high mortality rate. DAP's present late in their development and are unresectable in 30% of cases. The American Cancer Society estimates that there will be 28,600 new cases of pancreatic cancer in 1999 in USA, with 28,600 estimated pancreatic cancer deaths in the same year. These observations attest the inefficacy of current treatment modalities for this form of human cancer, and the limited knowledge of the pathogenic mechanisms leading to pancreatic cancer. These unsatisfactory results warrant a search for alternative treatments.

Additionally, colorectal cancer is a common neoplasm second only to lung cancer as the leading cause of death due to cancer in the United States. Advanced colon cancer is refractory to most chemotherapeutic agents. 5-Fluorouracil (5 FU) remains the most effective single agent with a response rate of 10–20% further showing the need for alternative treatments.

In vitro and in vivo studies of ascorbyl esters as antiproliferative compounds showed with preliminary results. For example, Ascorbyl esters have been found to inhibit cell proliferation and DNA synthesis of breast, skin, and brain tumors. These compounds are lipophilic, non-toxic, and can easily enter the intracellular compartment. However, there has been no study establishing any apoptotic activity for these ascorbyl esters.

Aberrant expression of IGF1 and IGF1-R has recently been reported in several human pancreatic cancer cell lines and in cancer cell lines and in cancerous human pancreatic tissues. It seems that the autocrine interaction between the IGF1-R and its ligand regulates both autonomous, anchorage-independent growth, and tumorigenicity of pancreatic carcinoma cells[9-10]. It would therefore be useful to develop a method and composition which regulates the expression of IGF1 and IGF1-R, thus causing apoptosis of these cancer cell lines.

L-Ascorbyl 6-palmitate (As-P), a synthetic lipophilic derivative of ascorbic acid, is widely used as a food additive to retard the development of oxidative rancidity in high-fat foods. Other useful functions as As-P in foods are: preventing nitrosamine formation while bacon is fried, conditioning yeasted doughs, lengthening shelf-life of bread and emulsifying carotinoid pigments. Besides its antioxidant activity, a few studies suggested that As-P may also possess antitumor activity in glioma cells.

It would therefore be useful to determine a method and composition for use in cancers. It would also be useful to develop a method and composition with an increased response rate for the treatment of cancer.

SUMMARY OF THE INVENTION

According to the present invention, there is provided a method of treating cancer by treating the cancer cells with a lipophilic synthetic derivative of ascorbic acid. Also provided is a method of inhibiting the Ras pathway by administering a lipophilic derivative of ascorbic acid. A method of inducing apoptosis in cancer cells is also provided by treating cancer cells with a lipophilic derivative of Asc-S. A pharmaceutical composition for the treatment of cancer including pharmaceutically acceptable carrier for Asc-S is also provided.

DESCRIPTION OF THE DRAWINGS

The patent or application file contains at least one drawing executed in color. Copies of this patent or patent application publication with color drawing(s) will be provided by the office upon request and payment of the necessary fee.

Other advantages of the present invention will be readily appreciated as the same becomes better understood by reference to the following detailed description when considered in connection with the accompanying drawings wherein:

FIGS. 1A–C are graphs showing the dose dependent inhibition of PANC-1 cell proliferation following 24 hours of treatment with Asc-S, PANC-1 cells cultured in MEM±10% FBS;

FIGS. 3A and B are photographs showing apoptosis as evaluated by in situ immunohistochemical detection and quantification at a single cell level;

FIG. 4 is a graph showing the Asc-S induced inhibition of Ras expression following treatment of PANC-1 cells;

FIGS. 5A and B are graphs showing the effect of Asc-S on PDGF-R expression on PANC-1 cells evaluated by Western blot analysis;

FIGS. 10A through D are photographs showing apoptosis as evaluated by in situ immunohistochemical detection and quantification at a single cell level;

FIGS. 11A and B are graphs showing the effects of daily oral administration of Asc-S via gavage which increased the median survival of C57BL/6 mice bearing intracerebrally induced glioma compared to controls;

DETAILED DESCRIPTION OF THE INVENTION

Figure 1A:
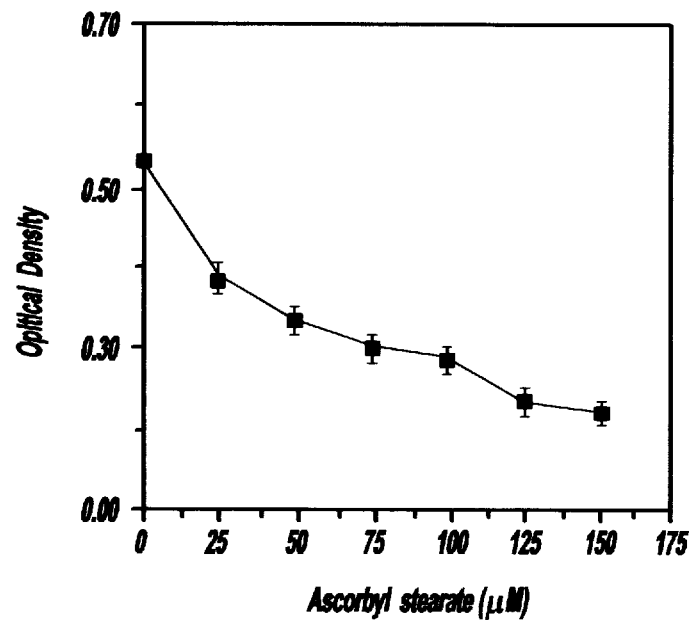

Generally, the present invention relates to a method and composition for treating cancer by treating the cancer cells with a lipophilic derivative of ascorbic acid. More specifically, the invention pertains to the use of lipophilic synthetic derivatives of ascorbic acid. Examples of such derivatives include, but not limited to, ascorbyl esters, ascorbic stearate or ascorbyl palmitate for the treatment of cancer in mammals. In the first preferred embodiment, Asc-S ascorbyl esters are used to treat pancreatic cancer. In the second preferred embodiment, Asc-P are used to treat colon cancer. In the third preferred embodiment Asc-S was used to treat brain tumors. In the fourth preferred embodiment Asc-S was used to treat ovarian cancer.

Ascorbyl esters have an inhibitory effect on cell proliferation and DNA synthesis in several tumor systems. Pauling (1991) reported the beneficial effect of high ascorbate dietary intake in preventing and/or delaying the spontaneous occurrence of breast tumors and UV light induced skin tumors in mice. Bishun et al (1978 and 1979) reported the antitumor activity of ascorbate using Hep2 and KB tumor cell lines. Ascorbyl esters are virtually non-toxic (LD50 of 25 g/Kg of Asc-S for mice) and are used a antioxidants. Ascorbate and stearic acid, the break down products of Asc-S are also non-toxic. Therefore, considering a lack of in vivo toxicity, prolonged treatment of patients (if necessary) with daily doses of Asc-S without known side effects is possible. The research clearly suggests that Asc-s induces apoptosis.

It has been established that the treatment of cells with Asc-S has an antiproliferative effect on PANC-1 and PC-1 cell lines derived from hamster and human pancreatic carcinomas. These antiproliferative and antitumorigenic effects of Asc-S as shown in pancreatic carcinoma, involve modifications of the IGF1/GF1R system, and facilitation of the apoptotic process. Considering the lack of in vivo toxicity of ascorbyl esters, even when used for prolonged time and at high doses, there is a showing of the efficacy of a new therapeutic modality for human pancreatic cancer, and other cancers, including lipophilic ascorbic acids.

In the laboratory experiments, Asc-S was administered subcutaneously at a dose of 100 mg/Kg body into BALB/c mice in the vicinity of the s.c. tumors. In addition, in a separate experiment involving intracerebral brain tumors in C57Bl/6, Asc-S was administered orally with gavage at a dose of 250 mg/kg of body weight. Further, more sophisticated methods of drug delivery, e.g., osmotic subcutaneous pumps, liposomal preparation for slow continuous release of Asc-S will be tested.

In the method of the present invention, the compound of the present invention can be administered in various ways. It should be noted that it can be administered as the compound or as pharmaceutically acceptable salt and can be administered alone or as an active ingredient in combination with pharmaceutically acceptable carriers, diluents, adjuvants and vehicles. The compounds can be administered orally, subcutaneously or parenterally including intravenous, intraarterial, intramuscular, intraperitoneally, and intranasal administration as well as intrathecal and infusion techniques. Implants of the compounds are also useful. The patient being treated is a warm-blooded animal and, in particular, mammals including humans. The pharmaceutically acceptable carriers, diluents, adjuvants and vehicles as well as implant carriers generally refer to inert, non-toxic solid or liquid fillers, diluents or encapsulating material not reacting with the active ingredients of the invention.

The doses may be single doses or multiple doses over a period of several days. The treatment generally has a length proportional to the length of the disease process and drug effectiveness and the patient species being treated.

When administering the compound of the present invention parenterally, it will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyols (for example, glycerol propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various of the other ingredients, as desired.

A pharmacological formulation of the present invention can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include: U.S. Pat. Nos. 5,225,182; 5,169,383; 5,167,616; 4,959,217;

4,925,678; 4,487,603; 4,486,194; 4,447,233; 4,447,224; 4,439,196; and 4,475,196. Many other such implants, delivery systems, and modules are well known to those skilled in the art.

A pharmacological formulation of the compound utilized in the present invention can also be administered orally to the patient. Conventional methods such as administering the compounds in tablets, suspensions, solutions, emulsions, capsules, powders, syrups and the like are usable. Known techniques which deliver it orally or intravenously and retain the biological activity are preferred.

In one embodiment, the compound of the present invention can be administered initially by intravenous injection to bring blood levels to a suitable level. The patient's levels can then be maintained by an oral dosage form, although other forms of administration, dependent upon the patient's condition and as indicated above, can be used. The quantity to be administered will vary for the patient being treated and will vary from about 100 ng/kg of body weight to 100 mg/kg of body weight per day and preferably will be from 10 mg/kg to 10 mg/kg per day.

The above discussion provides a factual basis for the use of ascorbic acid esters for the treatment of cancer. The methods used with and the utility of the present invention can be shown by the following non-limiting examples and accompanying figures.

EXAMPLE 1

PANC-1 Cell Culture: The human pancreatic ductal adenocarcinoma cell line PANC-1 was obtained from the American Type Culture Collection (Rockville, Md.). PANC-1 cells were cultured for 24 hours in Minimum Essential Medium (MEM) (Whitaker M A Bioproducts, Walkersville, Md.) supplemented with 10% fetal bovine serum (FBS) (Hyclone Laboratories, Logan, Utah) or serum free MEM+15 nM human recombinant IGF-1, penicillin (50 U/ml), streptomycin (50 $\mu$g/ml) and 1.0 mM L-glutamine.

Cell Growth and Vitality: The effect of Asc-S on PANC-1 and PC-1 cell growth and viability was evaluated by 3-(4, 5-dimethylthiazol-2yl)-2,5-diphenyl-tetrazoliumbromide (MTT) (Sigma Chemical Co., St. Louis, Md.) assay and the details of the procedure are as described earlier (Naidu et al., 1993a) PANC-1 cells were seeded at $2.5 \times 10^4$ viable cells well in 0.1 ml MEM supplemented with 10% FBS or serum free MEM with 15 nM human recombinant IGF-1 in 96 multiwell tissue culture plates. The following day when the cells were nearly confluent, the medium was replaced with fresh medium and 50, 75, 100, 125, 150, 175 and 200 $\mu$M Asc-S were added and incubated in a $CO_2$ incubator at 37° C. for 24 hours with respective untreated controls.

Effect of Asc-S on IGF1-R, and Ras expression by Western immunoblotting: This experiment was designed to test the hypothesis that significant inhibition of PANC-1 cell proliferation, after exposure to Asc-S, may be mediated through modulation of IGF1-R expression. PANC-1 cells were cultured for 24 hours in MEM+10% FBS and treated with 150 $\mu$M Asc-S for 24 hours, Asc-S treated and untreated (control). PANC-1 cells were analyzed by Western immunoblotting as follows: Cell lysates of treated and non-treated PANC-1 cells were obtained. The lysates were sonicated, centrifuged and protein concentration was determined with Pierce BCA protein kit (Pierce Laboratories). A 20 $\mu$g of protein was loaded and resolved at 4% to 15% polyacrylamide gradient gel by sodium dodecyl sulfate-polyacrylamide gel electrophoresis (SDS-PAGE) and electroblotted onto a nitrocellulose membrane (PVDF). The membrane was immunoblotted with mouse anti-human IGF1-R antibodies to cross-react the 85 kDa $\beta$-subunit of the IGF1-R (Pharmingen, San Diego, Calif.) followed by anti-mouse horseradish peroxidase conjugated secondary antibody (ECL, Amersham Corporation, Arlington Heights, Ill.). Antigen bound to nitrocellulose membrane was detected with the ECL system (Amersham Corporation, Arlington Heights, Ill.). P6 cells (3T3 fibroblast cells, transfected with a CVN plasmid constituitively expressing human IGF1-R) were used as the positive control.

In additional experiments PANC-1 cells were cultured in MEM+10% FBS and treated with different concentrations of Asc-S (e.g. 50, 75, 100, 125, 150 and 200 $\mu$M) for 24 hours. Lysates from these cells were subjected to Western immunoblotting for detection of modifications in IGF1-R expression in relation to the dose of Asc-S used. PANC-1 cells were also treated with 150 $\mu$M Asc-S at different time points, e.g., 1, 3, 6, 12, and 24 hours to detect variations in time in IGF1-R expression.

Soft agar experiments: To test the hypothesis that treatment of PANC-1 cells in culture with Asc-S reverses their transformed phenotype, the growth of PANC-1 was assessed in soft agar. PANC-1 cells were seeded at a density of $3 \times 10^3/35$ mm plate in 10% serum on a top layer of 0.3% agar and a bottom layer of 1% agar with and without the addition of 150 $\mu$M of Asc-S for 24 hours. The Asc-S was added to the top layer every day. Colonies greater than 125 microns in diameter (or ten cells) were counted at weekly intervals for 14–21 days. The clonogenicity was determined in three independent experiments comprising six replicates.

Detection of Apoptosis By In Situ Hybridization Using TUNEL Reaction: Apoptosis was determined by TdT-mediated dUTP nick end labeling (TUNEL) using an in situ cell death detection kit (Boehringer Mannheim, Indianapolis, Ind.). Asc-S treated and untreated PANC-1 cells were trypsinized and cytospin preparations were obtained. Cells were fixed with paraformaldehyde (4% in PBS, pH 7.4). After a rinse in PBS, the slides were incubated in permeabilization solution. Slides were cross-reacted with TUNEL reaction mixture for 60 minutes at 37° C. in a humidified chamber. Slides were thoroughly rinsed and reacted with alkaline phosphatase substrate solution for five to ten minutes (Vector Laboratories, Burlington, Mass.). The slides were analyzed under light microscope. These experiments were performed in duplicate.

RESULTS

Asc-S inhibits PANC-1 cell proliferation: PANC-1 (FIGS. 1A and 1B) and PC-1 (FIG. 1C) cells cultured in minimum essential medium (MEM)+10% fetal bovine serum (FBS) and serum free MEM+15 nM human recombinant IGF-1 were observed. The PANC-1 cells were cultured for 24 hours in MEM+10% FBS and treated with 0 (untreated control), 50, 75, 100, 125, 150, 175, $\mu$M Asc-S. Cell proliferation was measured by MTT assay. Asc-S inhibited cell proliferation in a dose dependent manner.

Figure 1B:
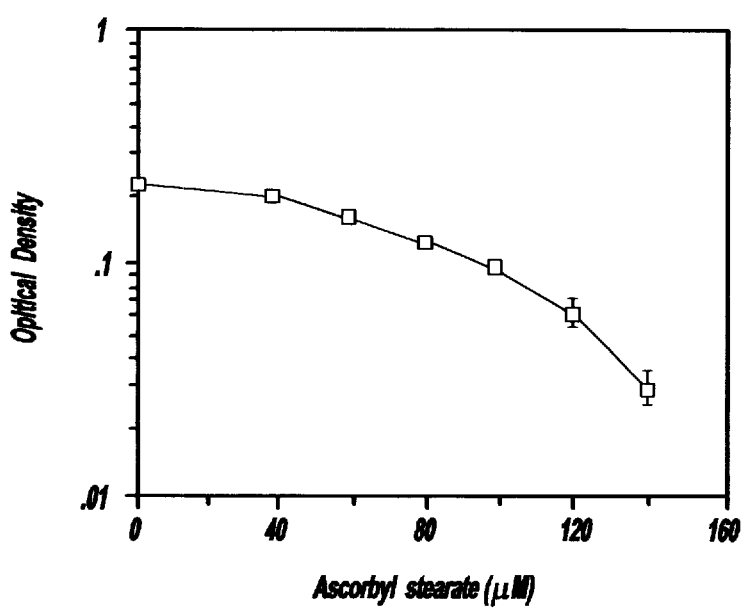

More specifically, FIGS. 1A and 1B show the dose dependent inhibition of PANC-1 cell proliferation following 24 hours treatment with Asc-S. PANC-1 cells were cultured in MEM+10% FBS, as depicted in FIG. 1A, or MEM+15 nM human recombinant IGF1 as, depicted in FIG. 1B, and exposed to different concentrations of Asc-S. FIG. 1C shows the dose dependent inhibition of PC-1 cell proliferation following 24 hours treatment with Asc-S. PANC-1 cells were cultured in MEM 15 nM human recombinant IGF-1 and exposed to different concentrations of Asc-S.

Treatment with Asc-S reduces the expression of IGF1-R: It was observed that PANC-1 and PC-1 cells cultured in either minimum essential medium (MEM)+10% fetal bovine serum (FBS) and/or serum free MEM+15 nM human recombinant IGF-1, when treated with Asc-S (150 μM) for 24 hours expressed a significantly lower number of receptors when analyzed by Western blotting, as compared to the untreated control. This inhibition was dose and time dependent. In fact the exposure of PANC-1 cells to different concentrations of Asc-S (e.g. 50, 75, 100, 125, 150, and 200 μM) for 24 hours in the same conditions, inhibited IGF1-R expression in a dose dependent fashion (FIG. 2A).

Figure 2A:
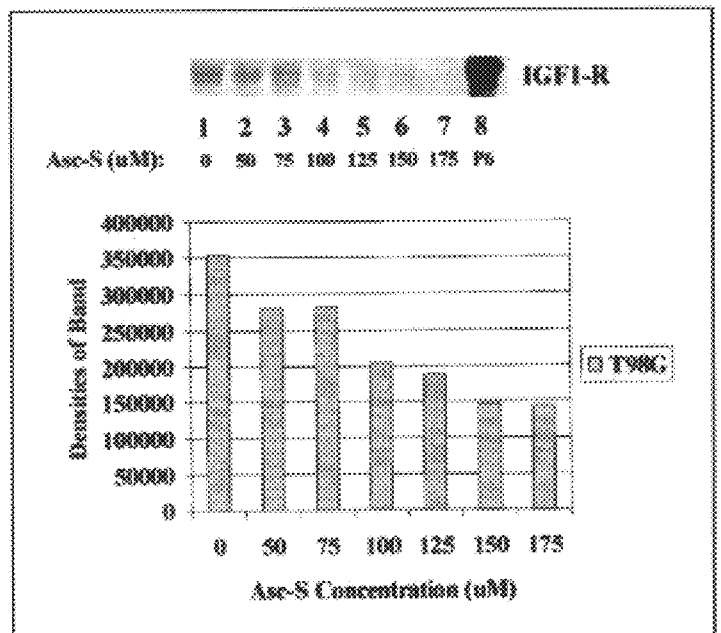
FIGS. 2A and B are graphs showing the Asc-S induced inhibition of IGF1-R expression following treatment of PANC-1 cells for 24 hours.
Figure 2B:
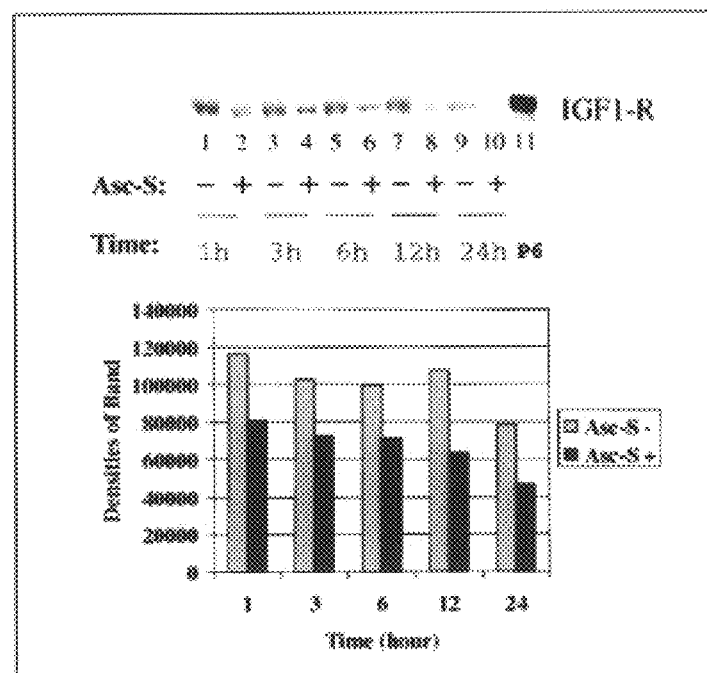
Figure 6:
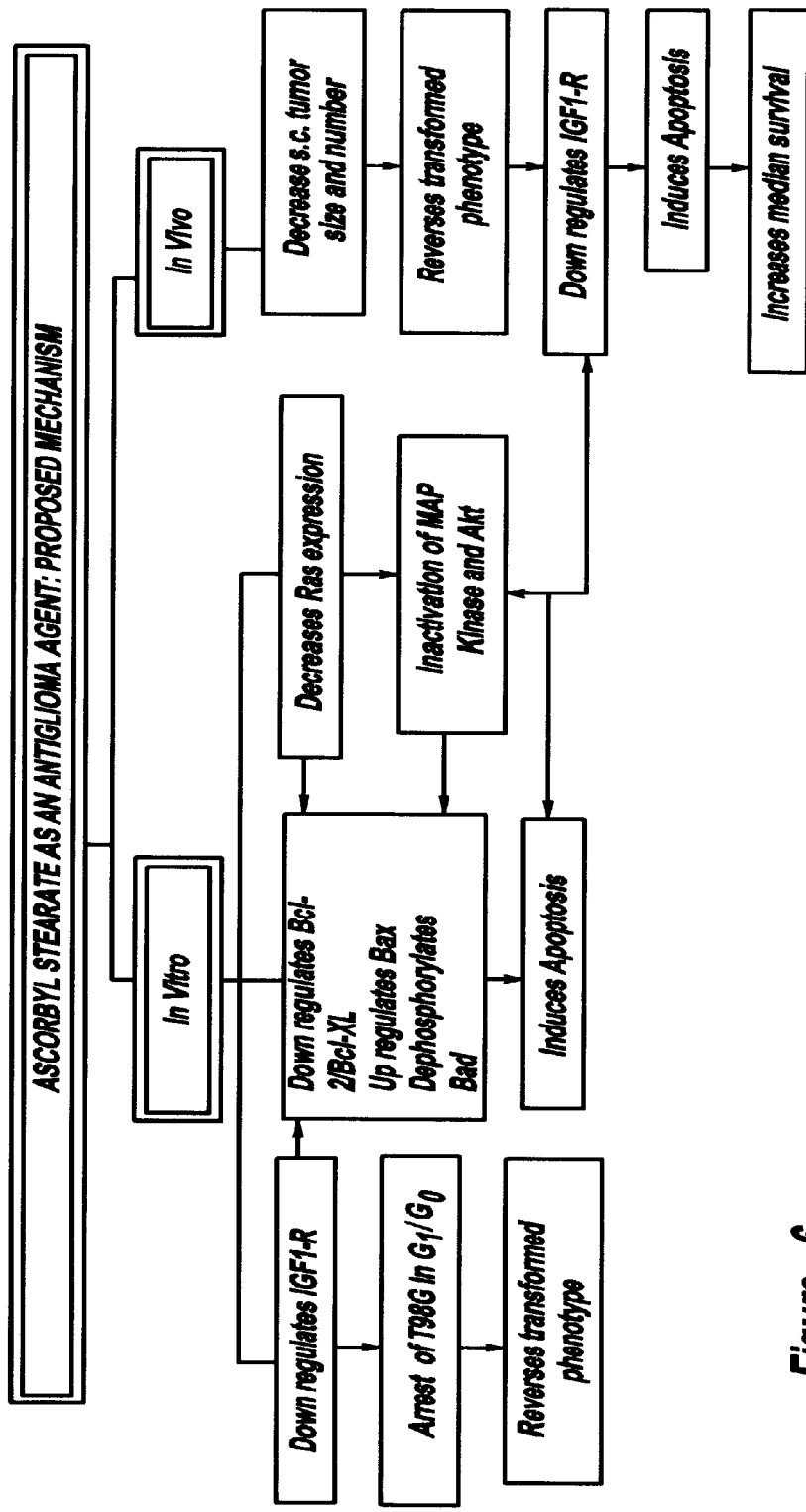
FIG. 6 shows the mechanism of action for ascorbic acid.

Similarly, the exposure of PANC-1 cells to 150 μM of Asc-S for different period of time, e.g. 1, 3, 6, 12 and 24 hours, inhibited the IGF1-R expression in a time dependent manner (FIG. 2B).

Specifically, FIGS. 2A and 2B showed that Asc-S induced inhibition of IGF1-R expression following treatment of PANC-1 cells for 24 hours with 150 μM. This inhibition was also dose and time dependent. FIG. 2A shows that Asc-S reduced IGF1-R expression of PANC-1 cells in a dose dependent fashion. In FIG. 2A there is shown the following: Lane1: untreated control; Lane 2: 50 μM Asc-S; Lane 3: 75 μM Asc-S; Lane 4: 100 μM Asc-S; Lane 5: 150 μM Asc-S; Lane 6: 200 μM Asc-S; Lane 7: P6 positive control for IGF1-R (these cells are 3T3 cells transfected with a plasmid constitutively expressing the human IGF1-R) which FIG. 2B shows that IGF1-R expressions of PANC-1 cells were inhibited by 150 μM Asc-S in a time dependent fashion. As in FIG. 2A, FIG. 2B shows the following: Lane 1: untreated control for 1 hour; Lane 2: PANC-1 treated with Asc for one hour; Lane 3: untreated control for three hours; Lane 4: PANC-1 cells treated with Asc-S for three hours; Lane 5: untreated control for six hours; Lane 6: PANC-1 cells treated with Asc-S for 6 hours; Lane 7: untreated control for 12 hours; Lane 8: PANC-1 cells treated with Asc-S for 12 hours; Lane 9: untreated control for 24 hours; Lane 10: PANC-cells treated with Asc-S for 24 hours; and Lane 11: P6 cells IGF1-R positive control.

Effect of Asc-S treatment on transformation of PANC-1 cells: To test the hypothesis that treatment of PANC-1 cells in culture with Asc-S reverses their transformed phenotype, PANC-1 cells were treated with 150 μM of Asc-S for 24 hours, and the untreated controls were tested for growth in soft agar. The Untreated controls were able to form more numerous and larger colonies as compared to the Asc-S treated PANC-1 (ratio 1:6) (see Table 1).

Apoptosis by in situ TUNEL assay: This experiment was designed to test the hypothesis that down regulation of IGF1-R can facilitate apoptosis in PANC-1 cells. PANC-1 cells treated with 150 μM Asc-S for 24 hours showed a significant increase in apoptosis as demonstrated by in situ TUNEL cell death assay (FIG. 3A). The untreated PANC-1 cells were negative for this test (FIG. 3B).

Specifically, FIGS. 3A and 3B showed that apoptosis was evaluated by in situ immunohistochemical detection and quantification at a single cell level. Treatment of PANC-1 cells with Asc-S (150, μM) induced apoptosis. FIG. 3A, a cytospin preparation of untreated PANC-1 cells, shows no staining for apoptotic cells. In FIG. 3B, a cytospin preparation of PANC-1 cells treated with 150 μM Asc-S for 24 hours, there is a significantly large population of apoptotic cells.

Effects of Asc-S on Ras expression in PANC-1 cells: The activation of the IGF1-R induces a cascade of phosphorylations including that of GDP to GTP with activation of the Ras pathway. If Asc-S induces a down regulation of the IGF1-R, Ras should consequently be affected. Indeed, PANC-1 cells treated with 150 μM Asc-S for 24 hours showed a significant inhibition in Ras (p21) expression by Western blot (FIG. 4).

FIG. 4 showed that Asc-S induced inhibition of Ras (p21) expression following treatment of PANC-1 cells for 24 hours with 150 μM Asc-S. Specifically, in FIG. 4A there is shown the following: Control: untreated PANC-1 cells; Asc-S: PANC-1 cells treated with Asc-S (150 μM) for 24 hours FIG. 4B showed that Ras (p21) expression, quantified by densitometry, was significantly down regulated following exposure to the Asc-S.

Asc-S treatment does not modify PDGF-R expressions: The effect of Asc-S exposure on other cell membrane receptors with tyrosine kinase activity (ei. PDGF-R) was also tested. Treatment of PANC-1 cells with 150 μM Asc-S for 24 hours did not affect PDGF-R expression (FIG. 5) showing that the effect of Asc-S on the IGF1-R is specific.

Specifically, FIG. 5 showed the effect of Asc-S (150 μM) on PDGF-R expression on PANC-1 cells, evaluated by Western blotting analysis. FIG. 5A shows the positive control for PDFG-R. FIG. 5B depicted the untreated PANC-1 and FIG. 5C showed the Asc-S treated Panc-1 cells (150 μM) for 24 hours.

CONCLUSIONS

It has been established that the treatment of cells with Asc-S has an antiproliferative effect on PANC-1 and PC-1 cell lines derived from hamster and human pancreatic carcinomas. These antiproliferative and antitumorigenic effects of: Asc-S as shown in pancreatic carcinoma, involve modifications of the IGF1/IGF1R system, and facilitation of the apoptotic process. Considering the lack of in vivo toxicity of ascorbyl esters, even when used for prolonged time and at high doses, there is a showing of the efficacy of a new therapeutic modality for human pancreatic cancer including lipophilic ascorbic acids.

EXAMPLE 2

HT-29, a human colon adenocarcinoma cell line, and CCD 18, a normal colon fibroblast, were obtained from the American Type Culture Collection (Rockville, Md.). The cells were grown in RPM1 1640 medium containing HEPES (20 mM), fetal bovine serum (10%), sodium bicarbonate (1 g/L), and penicillin (10 U/ml), streptomycin (10 ug/ml) at 37° C. in 5% $CO_2$ humidified atmosphere.

The effect of various concentrations of As-P, ascorbate, palmitate or 5-fluorouracil (5 FU) on the viability and/or proliferation of HT29 or CCD 18 cells were evaluated. Cells were seeded in 96-well culture plates at $1\times10^4$ cells/well. The following day, As-P, ascorbate, palmitate or 5 FU were added at various concentrations. Cell viability was evaluated by the MTT assay 24 hours or 48 hours after the addition of the compounds. The effect of As-P on the cell cycle of HT29 cells was also investigated by flow cytometry.

HT29 cells were seeded into 25 $cm^2$ flasks at a density of $1\times10^4$ cells/ml. 72 hours after seeding, As-P was added to HT29 cells in culture at a final concentration of 50 μM, 100 μM, 150 μM. Control cells received medium only. After 24 hours of incubation, cells were harvested and processed for flow cytometry DNA analysis.

RESULTS

The effect of ascorbyl-palmitate (As-P) on the viability or growth of human colon carcinoma HT29 cells and normal colon CCD18 fibroblasts was investigated. Cell viability or growth was assessed by the MTT assay. In HT29 cells, As-P appeared to have a stimulatory effect on cell growth at lower concentrations (below 100 μM) and a cytotoxic effect at higher concentrations (above 100 μM). Exposure of HT29 cells to As-P (150 μM) for 24 hours and 48 hours inhibited cell growth by 73% and 89% respectively. Exposure of HT29 cells to 5-fluorouracil (5 FU) at a similar concentration for 24 hours and 48 hours inhibited cell growth by 14% and 40% respectively. As-P also had a stimulatory effect on normal colon CCD 18 fibroblasts at the lower concentrations. At the higher concentration (150 μM) an approximately 20% inhibitory effect was observed at 24 hours and 48 hours. When HT29 cells or CCD18 fibroblasts were exposed to either ascorbate or palmitate at similar concentrations and incubation times, no inhibitory effect was observed. When treated with 150 μM As-P, HT29 cells were decreased in S phase and $G_2$/M phase and concomitantly Increased in $G_0$/$G_1$ phase.

These results suggest that As-P can have both stimulatory and cytotoxic effects on colon carcinoma HT29 cells, depending on the concentration. At higher concentrations, As-P was more toxic to cancer cells (HT29) and less toxic to nonmalignant cells than 5 FU.

Figure 12A:
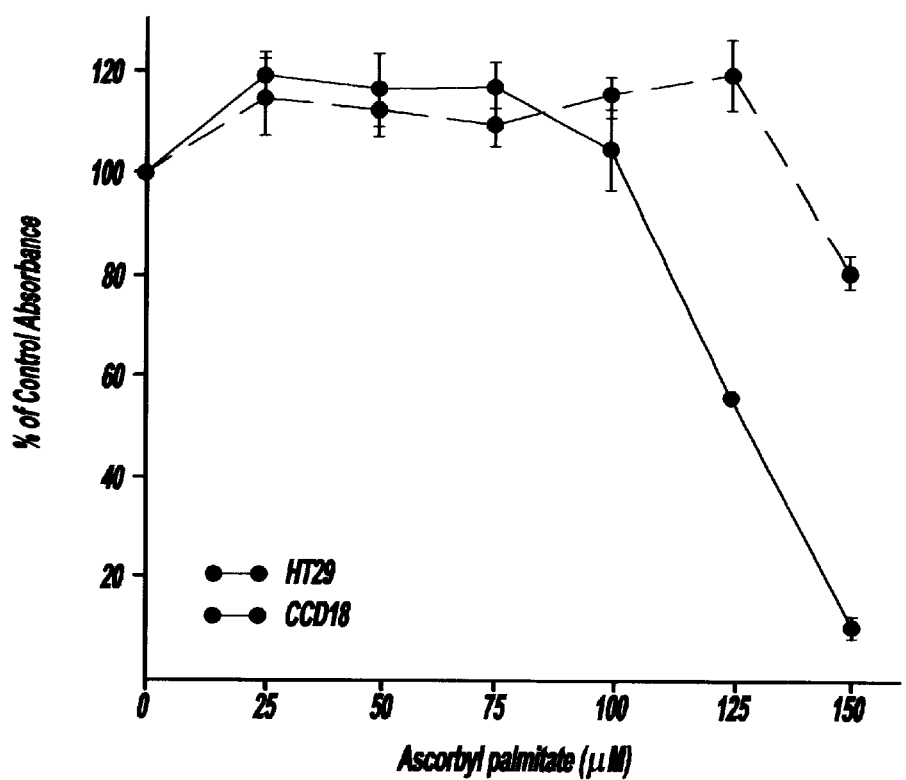
FIGS. 12A and B are graphs showing the effects of various concentrations of As-P on HT29 and CCD18 cell viability.
Figure 12B:
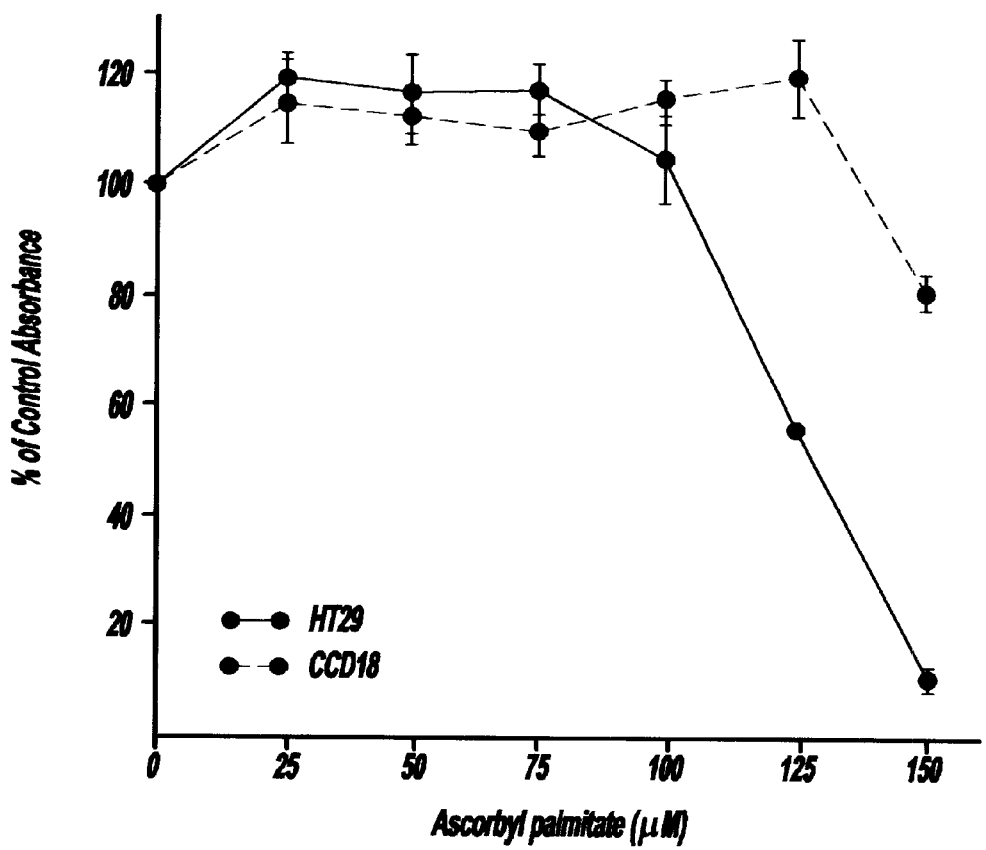

Specifically, FIG. 12 shows the effects of various concentrations of As-P on HT29 and CCD 18 cell viability (MTT assay). Cells were plated for 24 hours before they were treated with As-P for another 24 hours or 48 hours. Values are shown as means±S.D. of 2 experiments comprising 12 replicate samples.

Figure 13:
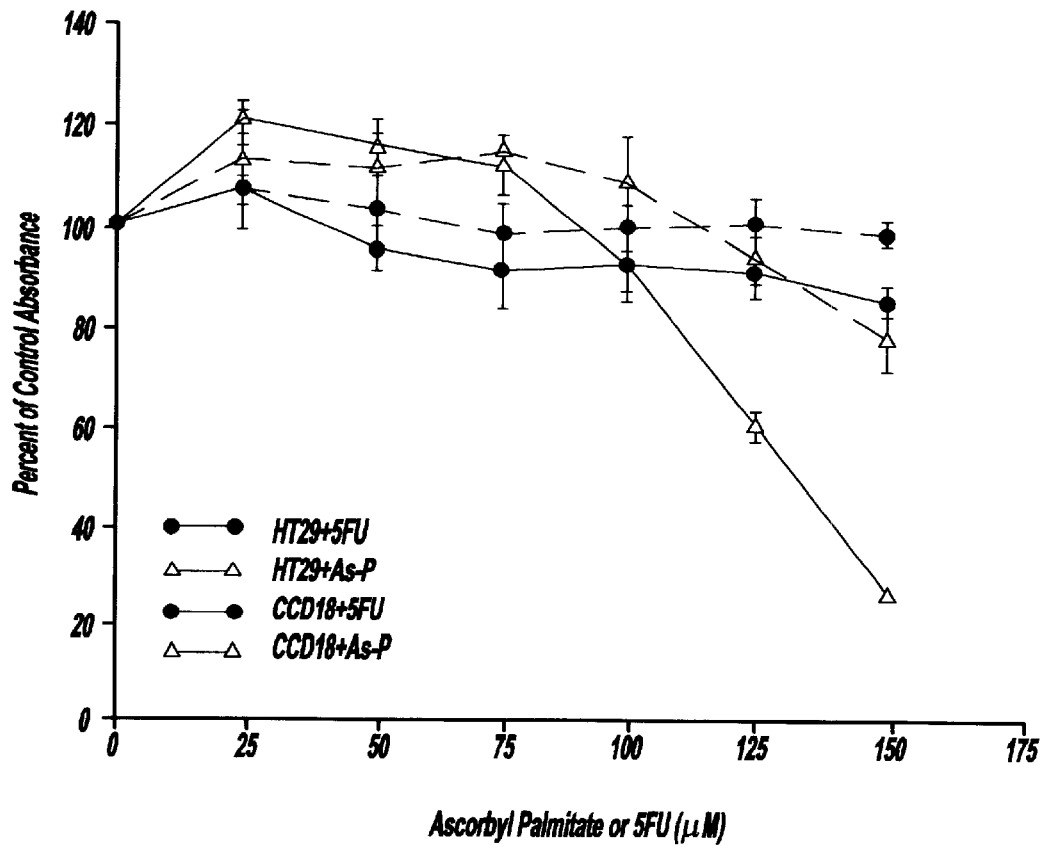
FIG. 13 is a graph showing the effects of various concentrations of 5 FU on HT29 CCD 18 cell viability.

Additionally, FIG. 13 shows the effects of various concentrations of 5 FU on HT29 and CCD 18 cell viability (MTT assay). Cells were plated for 24 hours before they were treated with 5 FU for another 24 hours or 48 hours. Values are shown as means±S.D. of 2 experiments comprising 12 replicate samples.

Figure 14A:
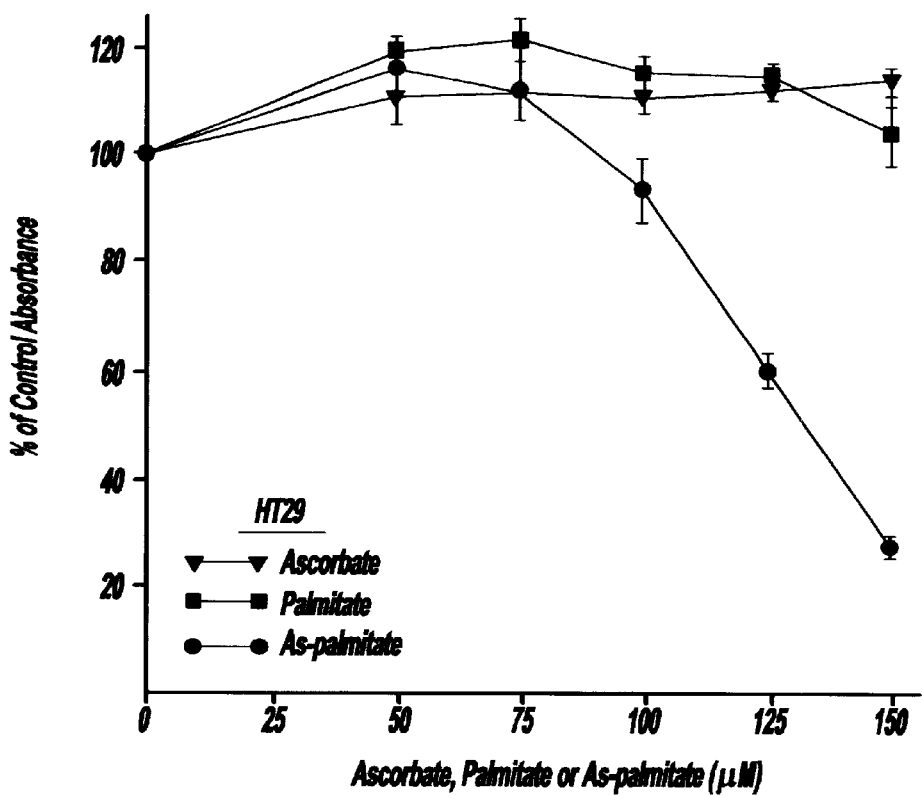
FIGS. 14A and B are graphs showing the effects of various concentrations of As-P ascorbate or palmitate on HT29 cell viability.
Figure 14B:
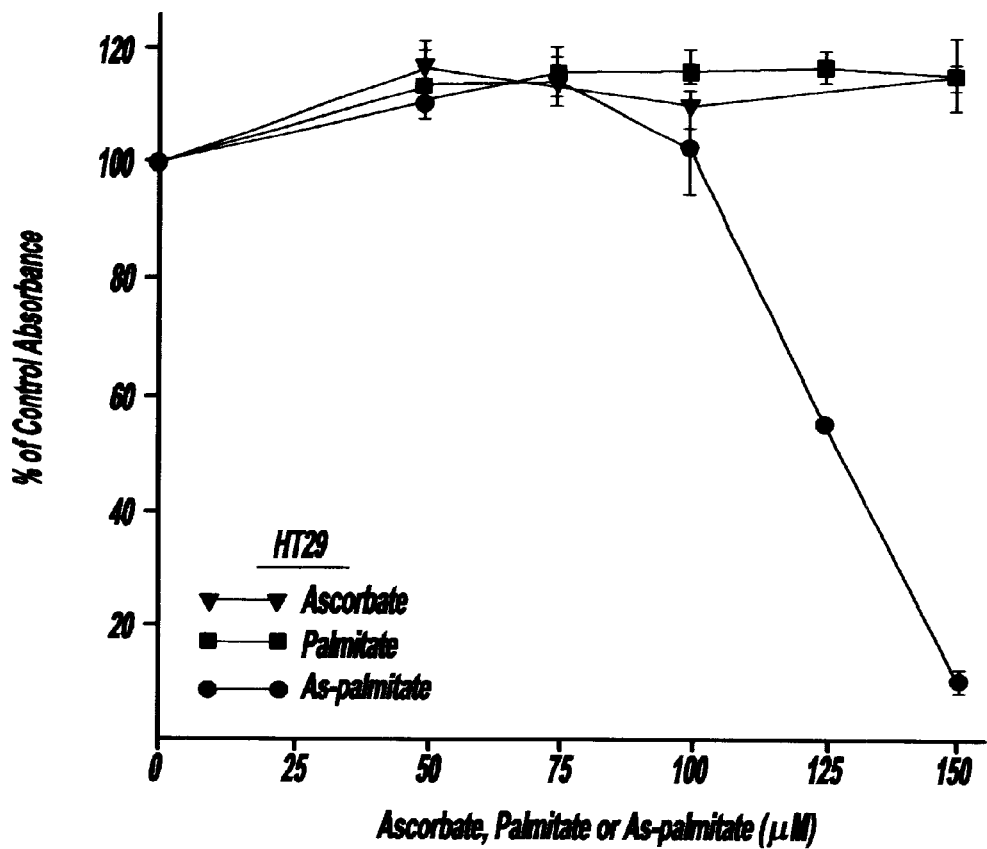

FIG. 14 shows the effects of various concentrations of As-P, ascorbate or palmitate on HT29 cell viability (MTT assay). HT29 cells were plated for 24 hours before they were treated with As-P, ascorbate or palmitate for another 24 hours or 48 hours. Values are means±S.D. of 2 experiments comprising 12 replicate samples.

Figure 15A:
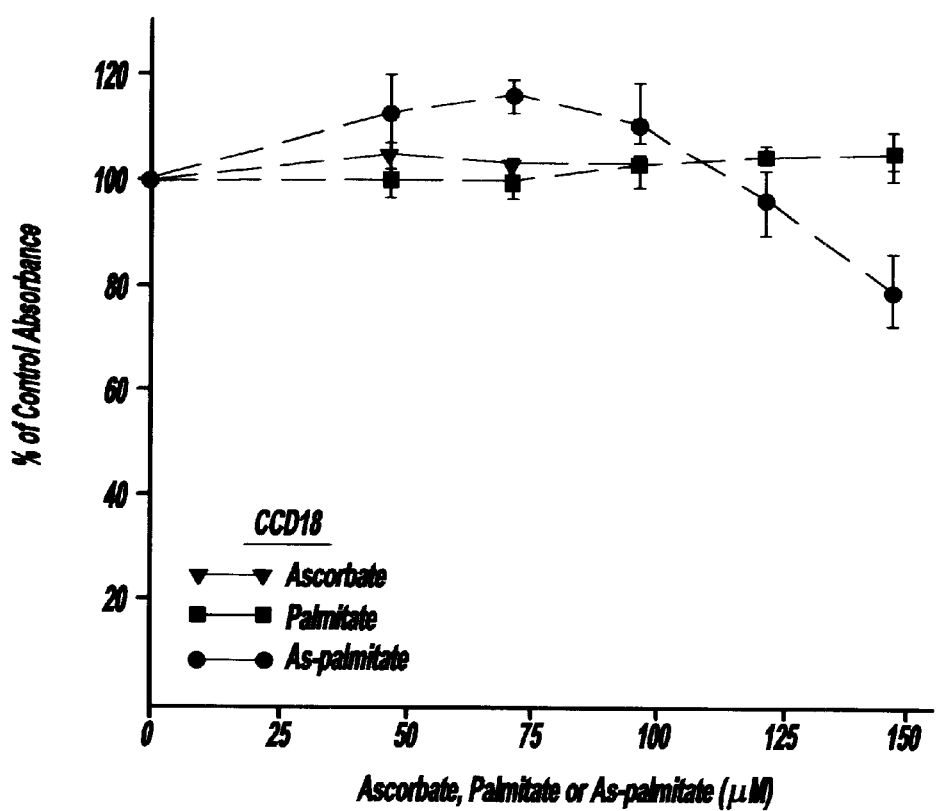
FIGS. 15A and B are graphs showing the effects of various concentrations of As-P ascorbate and palmitate on CCD 18 cell viability.
Figure 15B:
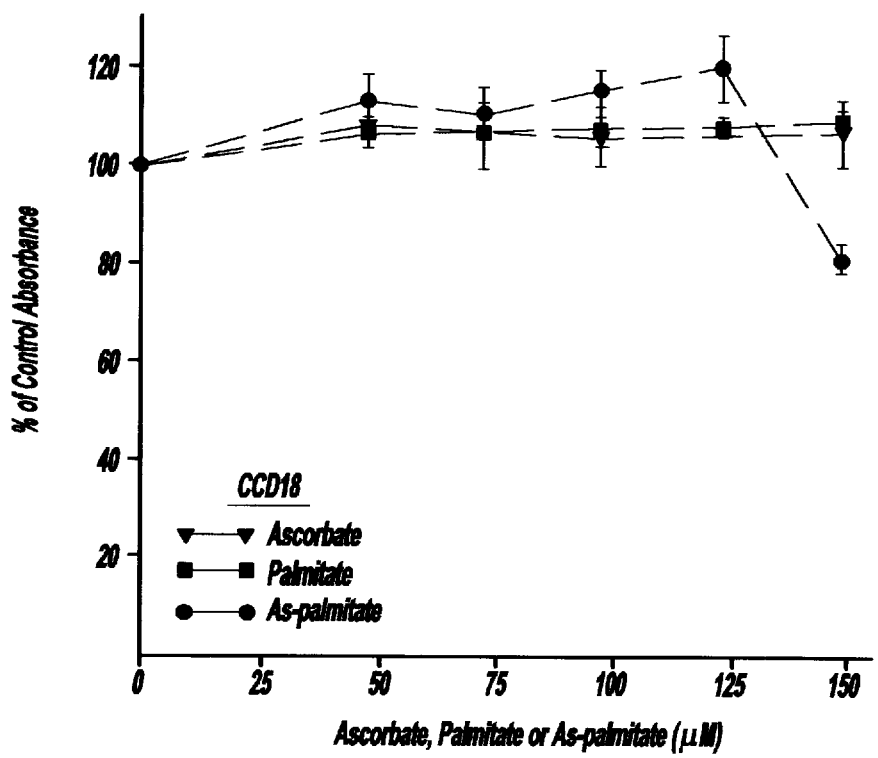
Figure 16:
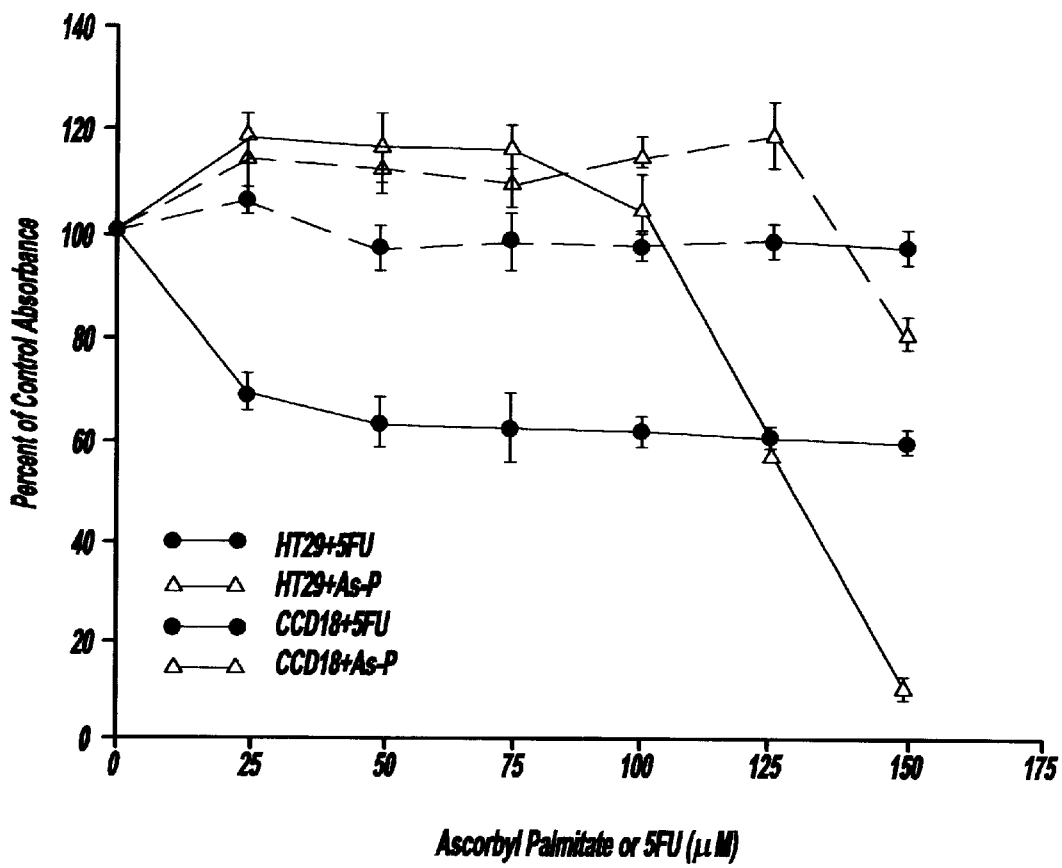
FIG. 16 is a graph showing the effects of various concentrations of ascorbyl palmitate or 5 FU on HT29 and CCD 18 cell viability.

FIG. 15 shows the effects of various concentrations of As-P, ascorbate or palmitate on CCD 18 cell viability (MTT assay). CCD18 cells were plated for 24 hours before they were treated with As-P, ascorbate or palmitate for another 24 hours or 48 hours. Values are means±S.D. of 2 experiments comprising 12 replicate samples.

Ascorbyl palmitate (As-P) showed a slight stimulating effect on HT29 cell growth at lower concentrations (<75 μM) and a great inhibitory effect at higher concentrations (>125 μM). Similar stimulatory effects were observed in CCD 18 (normal human colon fibroblasts), but the inhibitory effects were greatly reduced. At 24 hours, 5 FU had little or no inhibitory effect on the growth of HT29 colon cancer cells or CCD 18 normal colon fibroblasts. At 48 hours, 5 FU inhibited the growth of HT29 cells by approximately 40% but had little effect on CCD 18 cells. As compared to As-P, ascorbate or palmitate alone did not show inhibitory effect on HT29 and CCD 18 cell growth but had a slight stimulatory effect on HT29. Cells cycle analyses of HT29 cells after 24 hours exposure to As-P (>100 μM) showed an increase in the $G_0$/$G_1$ phase with a concomitant decrease in S and $G_2$+M phases.

EXAMPLE 3

Lipophilic derivatives of ascorbic acid, e.g., ascorbyl palmitate and ascorbic stearate (Asc-S), have a fatty acid moiety attached to ascorbate with an ester linkage. These compounds have a potent antiproliferative effect on human glioma, glioblastoma multiforme and colonic neoplastic cells in vitro and in vivo. The anti-proliferative effect of ascorbyl esters may be mediated through down regulation of insulin like growth factor-1 receptors (IGF-1R) and increased apoptosis. The data clearly shows that Asc-S induced down regulation of IGF1-R and thus triggers induction of apoptosis of human glioblastoma multiforme (T98G) cells through modifications in the apoptotic pathway (BC1-2, BC1-XL, Bax, Caspase-9 and Bad) and signaling pathway (Res, Akt and MAP kinases).

Ascorbyl esters were shown to inhibit cell proliferation and arrest cell multiplication cycle in G1/G0 phase of murine and human high grade gliomas in vitro and in vivo. Proliferation and tumorigenicity of human and murine glioblastoma cells are under the autocrine regulation of the IGF1/IGF1 receptor system. Based on the data obtained, the inhibition of glioma cell proliferation and tumorigenicity is induced by ascorbyl stearate (Asc-S) involves modification of the IGF1-R and facilitation of apoptosis. To test this hypothesis, the following in vitro and in vivo experiments were designed: the treatment of T98G cells with Asc-S (1) down regulates IGF1-R expression, arrests cells in G1/Go phase of the cell cycle and reverses the transformed phenotype; (2) induced inhibition of T98G cell proliferation via down regulation of IGF1-R is mediated through inactivation of down stream signaling proteins and kinases; Ras/c-Raf and Mitogen Activated Protein Kinase (MAP Kinase); (3) induces apoptosis, which are mediated through Bcl-Bcl-X, Bax, Bad and Akt expression; and (4) that subcutaneously implanted T98G cells in BALB/c nude mice, followed by treatment with Asc-S will have lesser, smaller sized tumors and longer median survival compared to the untreated controls.

EXAMPLE 4

Inhibition of cell proliferation induced by Asc-S, involves modifications of IGF1-R, and thereby lead to increased apoptosis. The inhibition of T98G cell proliferation observed in this study by Asc-S reflects a modulation in IGF1-R expression. The Asc-S could either induce a change in the IGF1-R expression or interfere with IGF1-R autophosphorylation and rendering the receptor non-functional, which leads to the facilitation of apoptosis.

T98G cell proliferation: Murine (G26) and human glioma (U-373) cell proliferation was inhibited following exposure to ascorbyl esters (Naidu et al., 1993a and 1993b). The cell proliferation was assessed by [$^3$H] thymidine incorporation and MTT assay (Naidu et al., 1993a, 1993b and 1996). These results were reproduced using T98G cells cultured with minimum essential medium (MEM)+10% fetal bovine serum (FBS) and serum free MEM+15 nM human recombinant IGF-1. The T98G cells were cultured for 24 hours in MEM+10% FBS, and, when confluent, were treated with 0 (untreated control), 50, 75, 100, 125, 150 and 175 μM Asc-S. Appropriate untreated controls were included. The cell proliferation was measured by MTT assay. Asc-S inhibited cell proliferation in a dose dependent manner (FIGS. 7A and B).

Figure 7A:
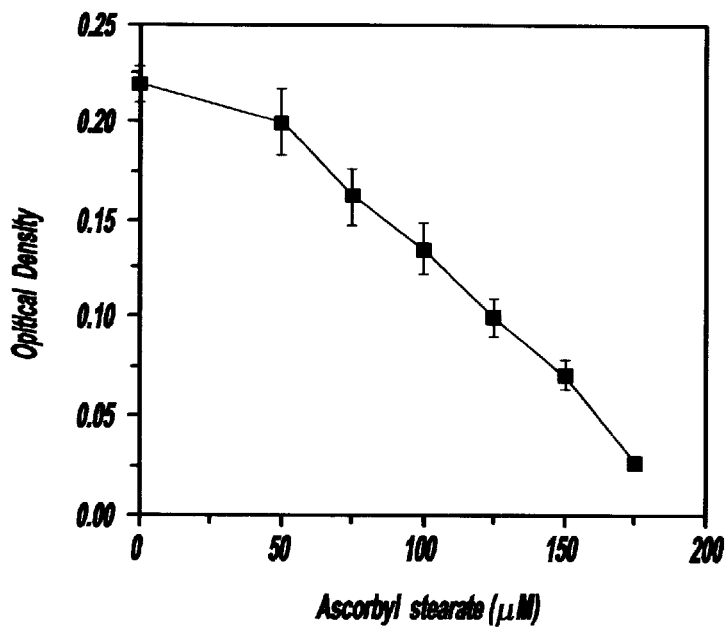
FIGS. 7A and B are graphs showing the dose dependent inhibition of T98G cell proliferation following 24 hours of treatment.
Figure 7B:
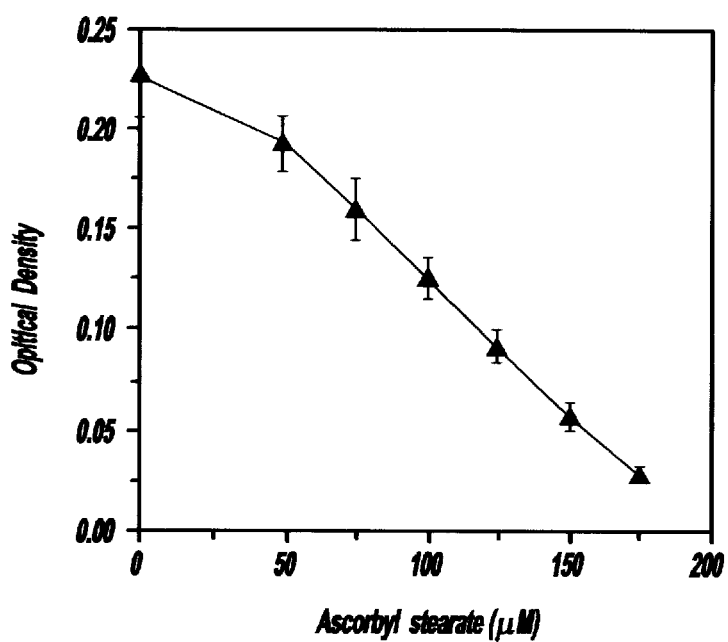

FIG. 7 shows the dose dependent inhibition of T98G cell proliferation following 24 hour treatments. Specifically, FIG. 7A shows T98G cells cultured in MEM+10% FBS and exposed to different concentration of Asc-S, and FIG. 7B shows T98G cells cultured in MEM+15 nM human recombinant IGF-1.

Figure 8A:
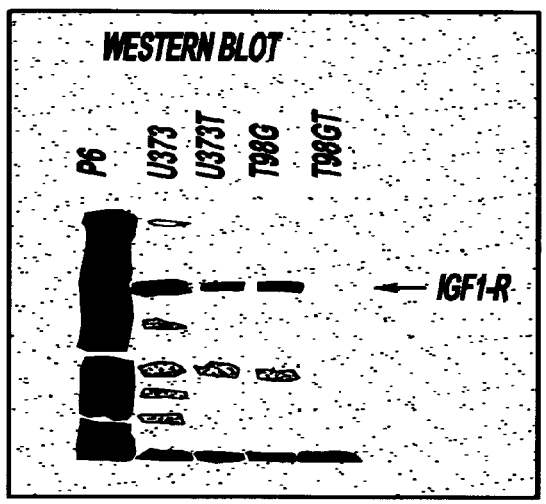
FIGS. 8A–D are graphs and photos showing the Asc-S induced inhibition of IGF1-R receptor expression following treatment of T98G.
Figure 8B:
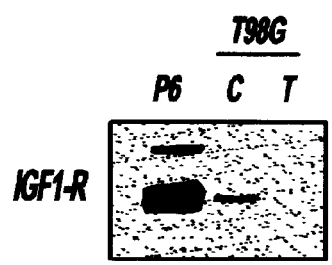
Figure 8C:
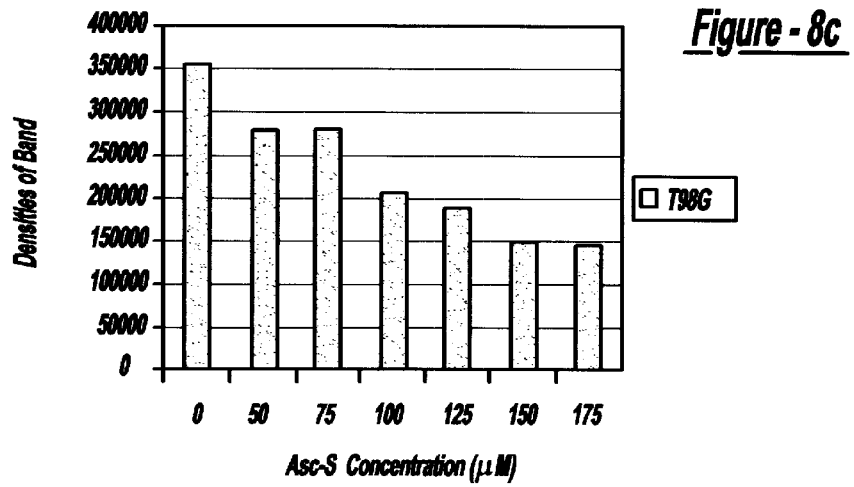
Figure 8D:
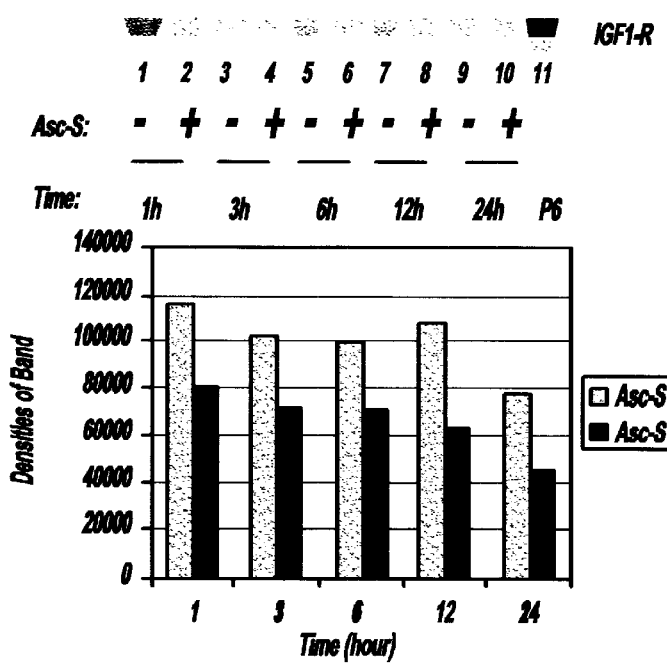

IGF1-R expression: This experiment was designed to test the hypothesis that significant inhibition of T98G and U-373 cell proliferation observed can be mediated through modulation in IGF1-R expression. The T98G and U-373 cells were cultured for 24 hours in MEM+10% FBS and when confluent were treated with 100 $\mu$M and 75 $\mu$M, Asc-S for 24 hours, respectively. As compared to the untreated cells, Asc-S treatment significantly down regulated IGF1-R expression, (FIGS. 8A and B). In addition, it was also observed that the inhibition of IGF1-R expression was dose and time dependent. The T98G cells culture in MEM+10% FBS and treated with different concentrations of Asc-S, e.g. 50, 75, 100, 125, 150 and 175 $\mu$M for 24 hours, inhibited IGF1-R in a dose dependent fashion (FIG. 8C). The T98G cells treated with 100 $\mu$M Asc-S for different time points, e.g. 1, 3, 6, 12 and 24 hours inhibited IGF1-R in a time dependent manner (FIG. 8D). IGF1-R expression was evaluated by Western immunoblotting technique with rabbit-antihuman IGF1-R antibodies (Upstate Biotechnology, Lake Placid, N.Y.) with HRP conjugated anti-rabbit secondary antibody.

More specifically, FIG. 8 shows that Asc-S induced inhibition of IGF1-R receptor expression following treatment of T98G and U-373 cells for 24 hours, with 100 $\mu$M and 75 $\mu$M Asc-S, respectively. The inhibition of IGF1-R expression was also dose and time dependent. FIG. 8A shows that IGF1-R expression was significantly decreased in Asc-S treated T98G and U-373 cells compared to untreated controls. Specifically, FIG. 8A shows the following: Lane 1: P6 positive control for IGF1-R, Lane 2: untreated U-373 cells; Lane 3: Asc-S (75 $\mu$M) treated U-373 cells; Lane 4: untreated T98G cells; Lane 5: Asc-S (100 $\mu$M) treated T98G cell; FIG. 8B shows that IGF1-R expression was significantly down regulated following treatment of T98G cells with 125 $\mu$M Asc-S for 24 hours. The following are depicted in FIG. 8B: Lane 1: P6 positive control for IGF1-R positive control for IGF1-R; Lane 2: untreated T98G cells; Lane 3: Asc-S (125 $\mu$M) treated T98G cells. FIG. 8C shows that Asc-S inhibited IGF1-R expression of T98G cells in a dose dependent fashion which is shown by the following: Lane 1: untreated control, Lane 2: 50 $\mu$M, Lane 3: 75 $\mu$M, Lane 4: 100 $\mu$M, Lane 5: 125 $\mu$M, Lane 6: 150 $\mu$M; Lane 7: 175 $\mu$M, and Lane 8: P6 positive control for IGF1-R. In FIG. 8D there is shown that IGF1-R expression of T98G cells was inhibited by 100 $\mu$M Asc-S in a time dependent fashion. Specifically, there is shown the following: Lane 1: untreated control for 1b, Lane 2: Asc-S treated for 1b, Lane 3: untreated control for 3b, Lane 4: Asc-S treated for 3b, Lane 5: untreated control for 6b, lane 6: Asc-S treated for 6b, Lane 7: untreated control for 12b, Lane 8: Asc-S treated for 12b, lane 9: untreated control for 24b, Lane 10: Asc-S treated for 24b, and Lane 11: P6 positive control for IGF1-R.

c-Src expression: To demonstrate that inhibition of IGF1-R expression observed in the present study is specific to Asc-S, the expression of ubiquotiously expressed c-Src was evaluated. The Src oncogene product was the first to be identified as tyrosine kinase. Today the "Src-family" of non-receptor tyrosine kinases is known to be represented in every cell type and signaling system. Treatment of T98G cells with 100 $\mu$M Asc-S for 24b did not affect the c-Src expression (FIG. 9), suggesting that the inhibition of IGF1-R expression observed is Asc-S specific. This observation is further corroborated with the data on the dose and time dependent inhibition of IGF1-R described herein.

Figure 9:
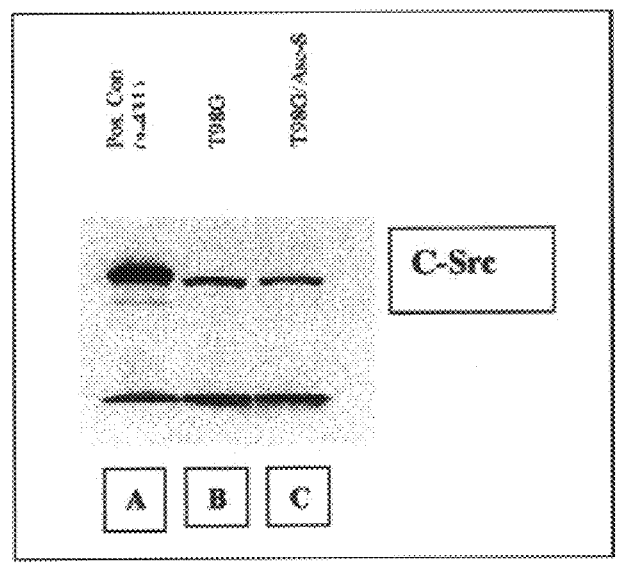
FIG. 9 is a photograph showing the effect of Asc-S on T98G cell c-Src expression evaluated by Western immunoblot analysis.

FIG. 9 shows the effect of Asc-S (100 $\mu$M) on T98G cell c-Src expression evaluated by Western immunoblot analysis. The T98G cells are exponentially grown in MEM with 10 nM human recombinant IGF-1 (Bachem California, Torrance, Calif.) or MEM with 10% FBS. The cells were disrupted in cold lysis buffer (10 $\mu$M terra sodium pyrophosphate, 20 mM HEPES, 1% Triton X-100, 100 mM NaCl, 2 ug/ml aprotinin, 2 $\mu$g/ml leupeptin and 100 $\mu$g/ml of PMSF). The crude lysates were centrifuged and protein concentration was determined by using Pierce BCA Protein Assay kit. Equal amounts protein (~25 $\mu$g) were placed in 2× sample buffer (0.135 M. Tris-HC1 [pH 6.8], 20% glycerol, 0.2 mg/ml bromophenol blue dye, 2% SDS and 10% B-mercapto-ethanol) and electrophoresed on a 10% SDS-PAGE electrophoretic gel (Novex, San Diego, Calif.). The proteins were then transferred to a nitrocellulose membrane by using electrobinding technique. Membranes were blocked for 30 minutes at room temperature in Tris buffer saline with Tween (TBST) and 5% nonfat milk. Rabbit anti-human polyclonal primary antibodies to c-Src ($pp_{60}^{Src}$ (aa403–421) (Upstate Biotechnology, Lake Placid, N.Y.) were incubated for one hour at room temperature in TBST and 1% nonfat milk. The blots were then washed and incubated with anti-rabbit horseradish peroxidase conjugated secondary antibody (Oncogene Science, Inc. Uniondale, N.Y.). Antigen bound to nitrocellulose membrane was detected with the ECL system (Amersham Corp., Arlington Heights, Ill.). FIG. 9A was a positive control for c-Src from A431 cell lysate, FIGS. 9B and C were untreated and 100 $\mu$M Asc-C treated T98G cell lysates respectively.

Apoptosis by in situ TUNNEL assay: This experiment was designed to test the hypothesis that down regulation of IGF1-R facilitates apoptosis in T98G cells. T98G cells treated with 100 $\mu$M Asc-S for 24 hours resulted in a significant increase in apoptosis as demonstrated by in situ TUNNEL cell death assay (Boehringer Mannheim, Indianapolis, IN). The untreated T98G cells were negative for this test (FIG. 9A), whereas T98G cells treated for 24 hours with 100 $\mu$M Asc-S showed a significant increase in apoptotic cells (FIG. 9B). In addition, to test whether Asc-S treatment induces apoptosis in normal cells, rat astrocyte cells in primary culture were treated with 100 $\mu$M Asc-S for 24 hours. The Asc-S did not increase the apoptotic rate (FIGS. 9 C and D) compared to untreated astrocytes. The increased apoptosis in the Asc-S treated T98G cells is due to down regulation of IGF1-R.

Figures 10A, 10B:
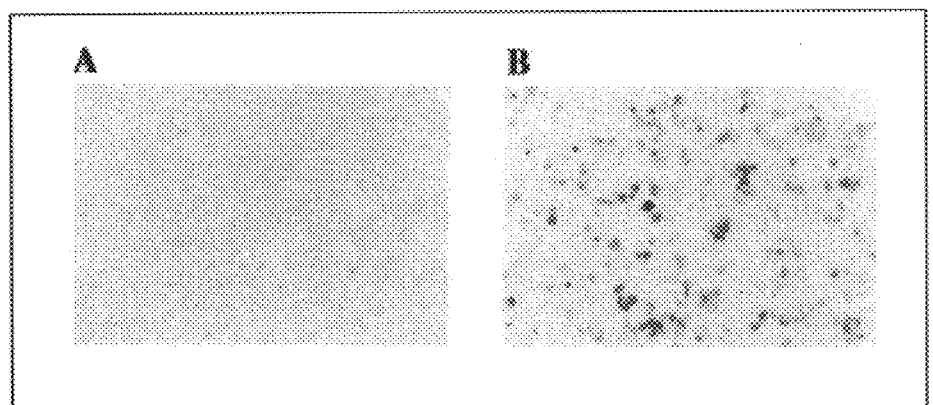

In FIG. 10, apoptosis was evaluated by in situ immunohistochemical detection and quantification at a single cell level. Treatment of T98G cell with Asc-S (100 $\mu$M) induced apoptosis, whereas, treatment of rat astrocytes with Asc-S (100 $\mu$M) did not induce apoptosis. In FIG. 10A, a cytospin preparation of untreated T98G cells, no staining for apoptotic cells was shown while in FIG. 10B, a cytospin preparation of T98G cells treated with 100 $\mu$M Asc-S for 24 hours, a significantly large population of apoptotic cells was shown. FIG. 10C shows a cytospin preparation of untreated rat astrocytes, which shows occasional apoptotic cells in a homogeneous population of astrocytes and FIG. 10D shows a cytospin preparation of rat astrocytes treated with 100 $\mu$M Asc-S for 24 hours, and therefore show occasional apoptotic cells, but nothing significantly different than the untreated controls.

In vivo administration of Asc-S (250 mg/Kg) on intracerebral gliomas in C57BL/6 mice: The C57BL/6 mice were implanted with mouse glioma cells (G-26) by stereotaxic intracerebral implantation. Preliminary data showed that the median survival of mice with intracerebral gliomas, treated with oral administration of Asc-S (250 mg/Kg body weight), was longer as compared to that of non-treated controls (43±2 days with Asc-S treatment vs 27±2 days with controls). (FIGS. 11A and B). These data indicate that treatment with Asc-S is effective in an in vivo model, which can be used to characterize the growth properties of tumor cells, and can lead to new therapeutic modality for high grade gliomas.

FIG. 11 shows the daily oral administration of Asc-S via gavage, increased median survival of C57BL/6 mice bearing intracerebrally induced glioma compared to controls (FIG. 11A). The body weight profiles of those mice during the experiments are shown in (FIG. 11B). The median survival observed in this study is statistically significant (P<0.05).

EXAMPLE 5

In Vivo Experiments Using BALB/c Nude Mice

The experimental approach is to test effect of Ascorbyl stearate (Asc-S) on the tumorigenicity of ovarian and pancreatic tumor cells. Procedures involve culturing OVCOR-3 (ovarian cancer cells) and PANC-1 (pancreatic cancer cells). When confluent, cells were trypsinized, washed and resuspended in sterile phosphate buffered solution (107) in a volume of 0.1 ml and injected s.c. above the hind leg of the mice. Two groups each for OVCOR-3 and PANC-1 tumor cells were established.

Reconstitution of Asc-S

Asc-S is lipophilic compound. Asc-S was dissolved in a small volume of ethyl alcohol and then reconstituted in sterile normal saline. The final concentration of ethyl alcohol was ~5%. At that concentration ethyl alcohol would not have any deleterious effect. In cell culture experiments similar concentrations were used and did not have any deleterious effects of the OVCOR-3 and PANC-1 tumor cells in culture. The controls received 50 ml of a mixture of 0.5:10 ethyl alcohol and sterile normal saline.

OVCAR-3 Cells

Group 1 is made up of OVCAR-3 cells plus Vehicle. A mixture of 0.5:10 of ethyl alcohol and normal saline was used as the vehicle. Group 2 is made up of OVCAR-3 cells plus Asc-S at a concentration of 100 mg/Kg was administered subcutaneously at the vicinity of the s.c. tumor one week prior to treatment with Asc-S. The Asc-S was distributed in a small volume of ethyl alcohol and then reconstituted into normal saline. The final concentration was 0.5:10 of ethyl alcohol and normal saline. Mice were treated daily with Asc-S for two weeks.

PANC-1 Cells

Group 1 is made up of PANC-1 cells plus a Vehicle. A mixture of 0.5:10 of ethyl alcohol and normal saline was used as the vehicle. Group 2 is made up of PANC-1 cells plus Asc-S at a concentration of 100 mg/Kg was administered subcutaneously at the vicinity of the s.c. tumor one week prior to treatment with Asc-S. The Asc-S was distributed in a small volume of ethyl alcohol and then reconstituted into normal saline and the final concentration was 0.5:10 of ethyl alcohol and normal saline. Mice were treated daily with Asc-S for two weeks.

Results

For the preliminary studies, six mice per group were used. The mice were administered with Asc-S for seven days following the induction of s.c. tumors. These mice were treated for two weeks with 100 mg of Asc-S/Kg body weight of mice. Mice receiving daily administration of Asc-S had decreased sized tumors compared to the untreated ones. There was a 70% decrease in the size of the tumors compared to the untreated controls. The s.c. tumors were isolated, tumor sizes were measured and processed for pathological evaluation. The pathological evaluation revealed that those s.c. tumors which were treated with Asc-S had a predominantly higher percentage of apoptotic cells compared to the untreated controls. This corroborates the in vitro data that this compound induces apoptosis in tumor cells thereby decreasing the tumor cell growth.

Since the preliminary results are encouraging, a large group of mice and different doses of Asc-S will be tested. A more detailed pathological analysis will be done to characterize the tumor. Also more sophisticated methods of drug delivery, e.g., osmotic subcutaneous pumps, liposomal preparation for slow continuous release of Asc-S will be tested.

EXAMPLE 6

Ductal adenocarcinoma of pancreas (DAP) is an aggressive exocrine pancreatic tumor with short median survival, and high mortality rate. Ascorbyl stearate (Asc-S) recently reported as antitumor agents, arrest the cell cycle in G0–G1 phase, suggesting the interaction with a progression growth factor. Aborrant expression of insulin-like growth factor receptor 1 (IGF1-R) has recently been reported in human pancreatic cancer. In this investigation the hypothesis that the antiproliferative action of Asc-S is mediated through decreased expression of the IGF1-R, with consequent facilitation of apoptosis was tested.

The effect of Asc-S on the proliferation of PC-1 and PANC-1 pancreatic tumor cells was studied using MTT assay. The expression of IGF1-R was analyzed by Western blot analysis, using polyclonal IGF1-R antibody (Upstate Biotech). Apoptosis was assessed by in situ hybridization using TUNEL reaction. The incubation of PC-1 and PANC-1 with increasing concentrations of Asc-S (50 to 200 $\mu$M), showed inhibition of proliferation in a dose dependent manner. This was associated with significant decrease in IGF1-R expression and increased apoptotic rate as compared to the control. Statistical analysis on the MTT assay was done using Student's T-test.

This data supports the antiproliferative effect of Asc-S on DAP. The mechanism of this action seems to involve modifications in IGF1-R expression, promoting programmed cell death.

EXAMPLE 6

Human glioma cell proliferation and tumorigrenicity are under autocrine control of the insulin like growth factor 1 (IGF-1) and its receptor (IGF-1R). Although it has been known for quite some time that ascorbic acid and its derivatives have anti-proliferative effects on various tumor cells, the precise mechanism of action is unknown. This study presents data on Ascorbyl Stearate (Asc-S) induced glioma (T98G) cell proliferation and transformation. Asc-S inhibited 10% fetal bovine serum (FBS) and human recombinant IGR-1 (10 $\mu$M) dependent T98G cell proliferation in a dose dependent manner. When cultured with FBS, a 8.7%, 38.5%, and 87.2% inhibition was observed with 50 $\mu$M, 100 $\mu$M and 175 $\mu$M Asc-S respectively. While with IGF-1, a 15.3%, 54.2% and 87.7% inhibition of T98G cell proliferation was observed with 50 $\mu$M, 100 $\mu$M and 175 $\mu$M Asc-S, respectively. This close dependent inhibition correlated with arrest of cell multiplication cycle in G1/Go phase. The Western immunoblot analysis of IGF-1 R expression revealed a significant inhibition of IGF-1 R following treatment with 100 $\mu$M Asc-S for 24 hours. The inhibition of IGF-1 Rs was also time and dose dependent.

As a corollary to the inhibition of proliferation and down regulation of IGF-1R, a significant increase in apoptosis was observed. Clonogenicity of T98G cells in soft agar following treatment with 100 μM Asc-S for 24 hours, lead to a significantly lost number of colonies (after three weeks, untreated Vs Asc-S treated T98G cells had a ratio of 40:1 colonies). It can be concluded that Asc-S induced inhibition of T98G cell proliferation, transformation and anchorage-independent growth involves modification in IGF-1R.

In vivo administration of Asc-S (250 mg/Kg) on intracerebral gliomas in C57BL/6 mice. The C57BL/6 mice were implanted with mouse glioma cells (G-26) by stereotaxic intracerebral implantation. Preliminary data showed that the median survival of mice with intracerebral gliomas, treated with oral administration of Asc-S (250 mg/Kg body weight), was longer as compared to that of non-treated controls ($43 \pm 2$ days with Asc-S treatment vs $27 \pm 2$ days with controls) (unpublished observation, FIGS. 17A and B). These data indicate that treatment with Asc-S is effective in an in vivo model, which can be used to characterize the growth properties of tumor cells, and can lead to new therapeutic modality for high grade gliomas.

Figure 17A:
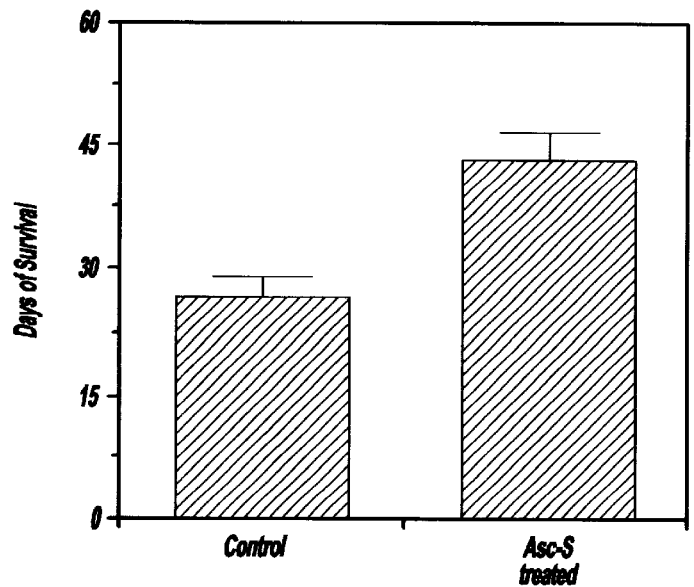
FIGS. 17A and B are graphs showing the effect of daily oral administration of Asc-S via gavage increased median survival of C57BL/6 mice bearing intracerebrally induced glioma compared to controls.
Figure 17B:
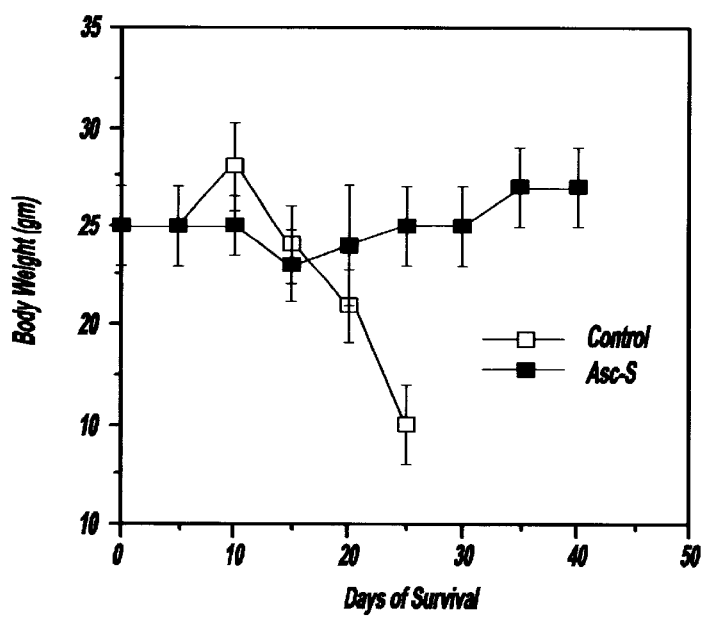

FIG. 17 shows that daily oral administration of Asc-S via gavage increased median survival of C57BL/6 mice bearing intracerebrally induced glioma compared to controls (FIG. 17A). The body weight profiles of those mice during the experiments are shown in (FIG. 17B). The median survival observed in this study is statistically significant ($P<0.05$).

Throughout this application, various publications, including United States patents, are referenced by author and year. Full citations for the publications are listed below. The disclosures of these publications in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

TABLE 1

Treatment of PANC-1 cells with 150 μM Acs-S reverses the transformed phenotype.

| Category | 1$^{st}$ week | 2$^{nd}$ week | r$^{rd}$ week |
|---|---|---|---|
| PANC-1 untreated | 39 colonies | 136 colonies | 252 colonies |
| Asc-S treated PANC-1 | 0 colonies | 15 colonies | 50 colonies |

TABLE 2

Cell cycle analysis of HT29 colon cancer cells exposed to various concentrations of As-P for 24 hours.
Cell cycle analysis of HT29 colon cancer cells exposed to various concentrations of As-P for 24 hr.

| Cell Cycle Phase | As-P Concentration | | | |
|---|---|---|---|---|
| | 0 μM | 50 μM | 100 μM | 150 μM |
| % G$_4$/G$_1$ | 55.3 | 57.1 | 73.1 | 86.1 |
| % S | 36.9 | 35.1 | 22.6 | 10.7 |
| % G$_2$ + M | 7.9 | 7.8 | 4.3 | 3.2 |

HT29 cells were seeded into 25 cm$^2$ flasks at a density of $1 \times 10^4$ cells/ml, 72 hrs after seeding, As-P was added to HT29 cells in culture at a final concentration of 50 μM, 100 μM, 150 μM. Control cells received medium only. After 24 hrs of incubation, cells were harvested and processed for flow cytometry DNA analysis.

REFERENCES

Korc M. Role of growth factors in pancreatic cancer. Surg Oncol Clin N Am 7:25–41, 1998.

Gudjonsson B, Livstone E M, Spiro H M. Cancer of pancreas. Diagnostic accuracy and survival statistics. Cancer 42:2494–2506, 1978.

Brooks J R, Culebras J M. Cancer of the pancreas, palliative operation, Whipple procedure, or total pancreatectomy. Am J Surg 131:516–519, 1976.

Landis S H, Murray T, Bolden S, et al. Cancer statistics, 1999. CA Cancer J Clin 49-8-31, 1999.

Pauling L. Effect of ascorbic acid on incidence of spontaneous mammary tumours and UV light induced skin tumors in mice. AM J Clin Nutr 54:1252S–1255S,1991.

Bishun N, Basu T K, Metcalfe S, Williams D C. The effect of ascorbic acid (vitamin C) on two tumor cell lines in culture. Oncology 35:160–162, 1978.

Bishun N. Williams D C, Basu T K, Metcalfe S. The effect of ascorbic acid on RNA and protein synthesis on two cultured cell lines in vitro. Cytobios 25:29–36, 1979.

Naidu A K, Wiranowski M, Kori S H, Roetzheim K C, and Kulkami A P. Inhibition of cell proliferation and glutathione S-transferase by ascorbyl esters and interferon in mouse glioma. J Neuro-Oncol 16:1–10, 1993.

Flossman-Kast B B M, Jeble M, Hoeflich A, Adler G, Lutz M P. Src stimulates insulin-like growth factor 1(IGF1)—dependent cell proliferation by increasing IGF-1 receptor number in human pancreatic carcinoma cells. Cancer Res 58:3551–3554, 1998.

Freeman J W, Mattingly C A, Strodel W E. Increased tumorigenicity in the human pancreatic cell line MIAPaCa-2 is associated with an aberrant regulation of the IGF-1 autocriac loop and lack of the expression of the TGF-beta type RII receptor. H Cell Physiol 165:163, 1995.

Baserga R. Controlling IGF-receptor function: a possible strategy for tumor therapy. Trends Biothechnol 14:150–152, 1996.

What is claimed is:

1. A method of treating cancer sensitive to an ascorbyl compound by treating the cancer cells with an effective amount of an ascorbyl stearate.

2. A method of claim 1 wherein the ascorbic acid is in a pharmaceutically acceptable carrier.

3. The method of claim 2, wherein the effective amount per dose is 100 ng/kg to 100 mg/kg based on the body weight of the patient.

4. A treatment for cancer sensitive to an ascorbyl compound by administering by administering to cancer cells an effective amount of a synthetic ascorbyl stearate.

5. The treatment of claim 4, wherein the cells are in vitro or in vivo.

6. The treatment of claim 5, wherein the cells are in vivo.

7. The treatment of claim 4, wherein the cells are in a mammal.

8. The treatment of claim 4, wherein the synthetic ascorbyl stearate is administered in the amount of at least 100 ng/Kg of body weight.

9. The treatment of claim 4, wherein the synthetic ascorbyl stearate is in a pharmaceutically acceptable carrier.

10. The treatment of claim 9, wherein the carrier is selected from the group consisting of pharmaceutically acceptable carriers, diluents, adjuvants, vehicles and implant carriers.

11. The treatment of claim 4, wherein the synthetic ascorbyl stearate is administered orally, subcutaneously, or parentally including intravenous, intraarterial, intramuscular, interaperitoneally, and intranasally as well as intrathecal and infusion techniques.

12. The treatment of claim 11, wherein the administration is done by a plurality of the dosing techniques.

13. The treatment of claim 4, wherein the administration is done with single or multiple doses.

14. The treatment of claim 4, wherein the administration is done by two or more dosing techniques.

15. A method of inhibiting the Ras pathway by administering an effective amount of an ascorbyl stearate.

16. A method of inducing apoptosis in cancer cells sensitive to an ascorbyl compound by treating cancer cells with an effective amount of an ascorbyl stearate.

17. The treatment of claim 4, wherein the cancer cells are selected from the group consisting of colon, brain, ovarian and pancreatic cancers.

* * * * *